United States Patent [19]
Honjo et al.

[11] Patent Number: 5,824,502
[45] Date of Patent: Oct. 20, 1998

[54] METHOD FOR SECRETORY PRODUCTION OF PROTEIN

[75] Inventors: Masaru Honjo; Naokazu Naito; Hiroshi Uchida, all of Chiba, Japan

[73] Assignee: Mitsui Chemicals, Inc., Tokyo, Japan

[21] Appl. No.: 825,217

[22] Filed: Mar. 27, 1997

[30] Foreign Application Priority Data

Mar. 28, 1996 [JP] Japan ................................. 8-074193

[51] Int. Cl.$^6$ .................................................. C12N 15/00
[52] U.S. Cl. .................. 435/69.1; 435/252.3; 435/320.1; 435/252.33; 536/23.1; 536/23.5; 530/350
[58] Field of Search ............................... 435/69.1, 252.3, 435/320.1, 252.33; 536/23.1, 23.5; 530/350

[56] References Cited

FOREIGN PATENT DOCUMENTS 0587427  3/1994  European Pat. Off. .
0735140 10/1996  European Pat. Off. .

OTHER PUBLICATIONS

Masuda et al. (1988) Biochim. et Biophys. ACTA, vol. 949, pp. 125–131.

Cheah et al. (1994) Gene, vol. 138, pp. 9–15.

Pogliano et al, "SecD and SecF facilitate protein export in *Escherichia coli*", *The EMBO Journal*, vol. 13, No. 3, 1994, pp. 554–561.

MacIntyre et al, "Requirement of the SecB chaperone for export of a non–secretory polypeptide in *Escherichia coli*". *Molecular and General Genetics*, vol. 27, 1991, pp. 224–228.

Nishiyama et al, "Disruption of the gene encoding p12 (SecG) reveals the direct involvement and important function of SecG in the protein translocation of *Escherichia coli* at low temperature", *The EMBO Journal*, vol. 13, No. 14, 1994, pp. 3272–3277.

Kihara et al, "FtsH is required for proteolytic elimination of uncomplexed forms of SecY, an essential protein translocase subunit", *Proceedings of the National Academy of Sciences USA*, vol. 92, May 1995, pp. 4532–4536.

Douville et al, "SecYEG and SecA are the stoichiometric components of preprotein translocase", *The Journal of Biological Chemistry*, vol. 270, No. 34, Aug. 25, 1995, pp. 20106–20111.

Tokuda, "Biochemical characterization of the presecretory protein translocation machinery of *Escherichia coli*", FEBS Letters, vol. 346, 1994, pp. 65–68.

Kary B. Mullis and Fred A. Faloona, "Specific Synthesis of DNA in Vitro via a Polymerase–Catalyzed Chain Reaction", *Methods in Enzymology*, vol. 155, 1987, pp. 335–350.

Naoki Masuda, Masanori Watahiki, Minoru Tanaka, Minoru Yamakawa, Ken Shimizu, Jun Nagai and Kunio Nakashima, "Molecular cloning of cDNA encoding 20 kDa variant human growth hormone and the alternative splicing mechanism", *Biochemica et Biophysica Acta*, 949, Jul. 21, 1987, pp. 125–131.

Julián Pérez–Pérez, Concepción Martínez–Caja, José Luis Barbero and Julio Gutiérrez, "DNAK/DNAJ Supplementation Improves the Periplasmic Production of Human Granulocyte–Colony Stimulating Factor In *Escherichia Coli*", *Biochemical and Biophysical Research Communications*, May 16, 1995, pp. 524–529.

Julian Pérez–Pérez, Gabriel Márquez, José–Luis Barbero and Julio Gutiérrez, "Increasing the Efficiency of Protein Export in *Escherichia coli*", *Bio/Technology*, Feb. 12, 1994, pp. 178–180.

Nancy G. Nossal and Leon A. Heppel, "The Release of Enzymes by Osmotic Shock from *Escherichia coli* in Exponential Phase", *The Journal of Biological Chemistry*, vol. 241, No. 13, Jul. 10, 1966, pp. 3055–3062.

Joseph A. Martial, Robert A. Hallewell, John D. Baxter, Howard M. Goodman, "uman Growth Hormone: Complementary DNA Cloning and Expression in Bacteria" SCIENCE1, vol. 205, 1979, pp. 602–607.

Hiroaki Inoue[a], Hiroshi Nojima[b] and Hiroto Okayama[b], "High efficiency transformation of *Escherichia coli* with plasmids", *GENE*, 96, Jun. 15, 1990, pp. 23–28.

Kanefusa Kato, Hideo Fukui, Yoshitaka Hamaguchi and Eiji Ishikawa, "Enzyme–Linked Immunoassay: Conjugation Of The FAB' Fragment Of Rabbit IgG with β–D–Galactosidase From *E. Coli* and Its Use For Immunoassay", *The Journal of Immunology*, vol. 116, No. 6, Jun. 6, 1976, pp. 1554–1560.

*Primary Examiner*—Rebecca E. Prouty
*Assistant Examiner*—Enrique D. Longton
*Attorney, Agent, or Firm*—Burns, Doane, Swecker & Mathis, L.L.P.

[57] ABSTRACT

Efficient secretory production of a recombinant protein in the periplasm can be attained by artificially regulating co-expression of a gene coding for the target recombinant protein and a gene coding for Sec protein involved in protein transport in *E. coli* cells under conditions in which excessive expression of the Sec protein is suppressed.

8 Claims, 7 Drawing Sheets

DNA sequence of proximal region of SecB gene

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATCAAGCTTA AGGGAATTGC CGTGT        25

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACTGAGCTCA AATCCCGATC TTCTGA        26

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TATGAATTCA TGAGTGCGAA TACCGAAGCT CAA        33

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AAACTCGAGT CACCTCAGGC CAGTGATAAA GGA        33

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

-continued

TTTCTCGAGA GGAAACAATG GCTAAACAAC CGGGATTAGA T    41

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TTTCTGCAGA TGCATTTATC GGCCGTAGCC TTTCAGGTT    39

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ACTGCTAGCG AAGATTGCCG GGAT    24

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TTCGCTAGCA GTATTATTCT GTACCCG    27

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CCATGATCAC GACAACAACG TTAAG    25

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGTGATCATG GACTTTATGG CTCAA    25

( 2 ) INFORMATION FOR SEQ ID NO:11:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

GTAGAATTCA TGTCAGAACA AAACAACACT 30

( 2 ) INFORMATION FOR SEQ ID NO:12:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:12:

CCAAGCTTTC TTGCCAGGGT 20

( 2 ) INFORMATION FOR SEQ ID NO:13:

( i ) SEQUENCE CHARACTERISTICS:
  ( A ) LENGTH: 85 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

ACAGAATTCC CGGGGATCCG TCGACCTGCA GTATTTAAGG ACAACACTTA AGGGTTTTCT 60

ACACATGTCA GAACAAAACA ACACT 85

( 2 ) INFORMATION FOR SEQ ID NO:14:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:14:

AGATCCGGAG CAAAAACAGG AAGGC 25

( 2 ) INFORMATION FOR SEQ ID NO:15:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:15:

TTTGAATTCC GCAAGGAACA GGTTG 25

( 2 ) INFORMATION FOR SEQ ID NO:16:

( i ) SEQUENCE CHARACTERISTICS:
  ( A ) LENGTH: 25 base pairs
  ( B ) TYPE: nucleic acid

```
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

TTTAAGCTTT TTAGTTCGGG ATATC                                    2 5
```

METHOD FOR SECRETORY PRODUCTION OF PROTEIN

BACKGROUND OF THE INVENTION

1. Field of the Invention

The present invention relates to a method for secretory production of useful proteins using *Escherichia coli*, and in particular relates to a method for the secretory production of recombinant proteins using *E. coli* transformants, in which a gene for a protein associated with membrane transport of proteins is co-expressed along with the target protein to attain highly efficient secretory production when the recombinant proteins are secreted and accumulated in the periplasm of *E. coli*.

2. Description of the Related Art

*E. coli* is often used for the production of useful proteins by recombinant DNA technology. Such methods for the production of proteins using *E. coli* are generally intracellular production methods and secretory production methods. Production efficiency in secretory production methods, is generally lower than that in intracellular production methods because a step of transport across membrane and a step of precarsor processing are additionally necessary. In particular, the production efficiency of secretory production in procaryotes such as *E. coli* is known to be much lower in the production of proteins derived from mammals than in the production of proteins derived from procaryotes. Therefore, development of an excellent secretory production method which is also applicable to production of proteins derived from mammals was being sought.

Established experimental methods in molecular genetics and experimental methods for plasma membrane transport have revealed that Sec proteins (e.g., SecB, SecA, SecD, SecF, SecE, SecY, SecG) are involved in membrane transport in protein secretion in *E. coli*.

SecB resides in the cytoplasm and acts as a so-called molecular chaperon to maintain many precursors in an appropriate form (unfolding form) for membrane transport by binding with the precursors. SecB is a chaperon specific to secretory proteins. Examples of other known general chaperons are GroEL, GroES, DnaK and DnaJ.

SecA is a membrane surface protein present in the cytoplasmic side of the plasma membrane and is an essential factor for membrane transport of secretory proteins. It is believed that SecA binds to a signal peptide which is present at the N-terminal of a precursor protein produced in the cytoplasm, and leads the precursor to the membrane transport apparatus. Furthermore, SecA has ATPase activity, which is essential in membrane transport, and has a role in initiating membrane transport by inserting the precursor protein into the plasma membrane.

SecE and SecY are also known to be essential factors in membrane transport like SecA. Both SecE and SecY are endogenous proteins residing in the plasma membrane and have function as a complex. Further, since SecY is an unstable protein, a complex form with SecE, i.e., expressed as SecE/Y, is occasionally treated like a single factor. Also, reconstruction of ATPase activity of SecA is known to require the three factors, SecA, SecE and SecY.

SecG is involved in activation of the SecA-SecE-SecY complex which is an essential factor for membrane transport, and is known to be essential in low temperature *E. coli* growth and in protein secretion.

Both SecD and SecF are known to be endogenous proteins residing in the plasma membrane, and the majority of their molecules is present in the periplasm side of the plasma membrane. Since SecD and SecF form an operon, i.e., expressed as SecD/F, they are treated as a single factor. It has been suggested that SecD is involved in liberation of secretory proteins from the membrane, which is the final step of membrane transport. The function of SecF is not known but is thought to function similar to SecD.

Thus, it is clear that Sec proteins are involved in protein secretion and in the membrane transport mechanism in *E. coli*. However, although there have been many attempts, only a few examples of actual applications of these Sec proteins to secretory production of useful proteins are known.

One such example is a report on secretory production of interleukin 6 (IL-6) in *E. coli* (BIO/TECHNOLOGY, 12, 178–180, 1994). In this report, *E. coli* cells were transformed by two kinds of plasmid, i.e., one in which SecE, SecY (also called prlA), prlA4 (a variant protein of SecY) genes, alone or in combination, were incorporated into an expression vector, and the other containing IL-6 gene, and then the level of secretory production of IL-6 by the resulting transformed *E. coli* cells was compared. Results showed that when SecE gene in combination with prlA4 gene was co-expressed, IL-6 secretion efficiency was markedly improved, but when SecE gene or prlA4 gene alone was co-expressed, IL-6 secretion efficiency was hardly improved at all. When SecY gene in combination with SecE gene was co-expressed, IL-6 secretion efficiency was conversely reduced.

Furthermore, the same researchers have reported on secretory production of granulocyte colony stimulating factor (G-CSF) in *E. coli* (Biochem. Biophys. Res. Commun., 210(2), 524–529, 1995). In this report, plasmids containing a single or a multiple number of chaperons, i.e., SecB, GroES, GroEL, DnaK and DnaJ genes, were constructed, and *E. coli* cells transformed by these plasmids were cultured to compare the effect of co-expression of these chaperon genes on G-CSF secretory production. Results showed that when DnaK or DnaJ gene alone was co-expressed, processing of precursors was slightly improved and when DnaK gene in combination with DnaJ gene was co-expressed, the effect on secretory production was most remarkable. In contrast, no effect was observed when SecB gene alone or GroEL/GroES chaperon genes were co-expressed. Furthermore, in an analogous manner, the same researchers at the same time studied the effect of co-expression of the above-mentioned various chaperon genes on IL-6 secretory production and reported that no effect was observed.

The abovementioned reports show that secretion efficiency cannot always be improved by simply co-expressing genes of Sec proteins.

That is, there is no guide to know how these Sec protein genes, whose contribution in membrane transport has been proved in vitro, should be expressed in order to improve secretion efficiency. The abovementioned report (BIO/TECHNOLOGY, 12, 178–180, 1994) is an extremely rare successful example of the use of the variant of SecY (prlA4). Furthermore, in this example, *E. coli* cells transformed by two different plasmids (a plasmid containing SecE/prlA4 genes and a plasmid containing IL-6 gene) were used. Since it is generally difficult to consistently control the number of copies of plasmids in the cells transformed by the two different plasmids because of incompatibility between the plasmids, protein productivity becomes unstable, which causes a serious problem in an industrial application.

SUMMARY OF THE INVENTION

Objectives of the present invention are to provide plasmids which can be used for highly efficient secretory production of useful proteins in microorganisms, which has so far been difficult, to provide E. coli transformants transformed by said plasmids, and to provide a method for secretory production of recombinant proteins using said E. coli transformants.

The present inventors constructed various plasmids in which Sec protein genes can be co-expressed with target protein genes, and transformed E. coli cells with said plasmids to compare their efficiency in secretion of the target proteins in the periplasm. Surprisingly, it was found to be very important to control excessive expression of Sec protein genes and secretion efficiency of target proteins can be improved only with an appropriate level of co-expression of Sec protein gene, wherein this invention was completed. It is impossible to predict from previously reported results of in vitro experiments that the level of expression of Sec protein genes has a great effect on improving the secretion efficiency of target proteins. Furthermore, there is no mention in the abovementioned reports as to the effect of the level of Sec protein gene expression on efficiently secretory production of IL-6 and G-CSF.

Thus, the present invention provides recombinant plasmids which contain a protein gene and at least one Sec protein gene derived from E. coli, selected from the group consisting of genes of SecB, SecD/F, SecG and SecE/Y, and further contain a DNA fragment which suppresses excessive expression of said Sec protein gene; E. coli transformants obtained by transformation with said recombinant plasmids, characterized in that the protein gene and the Sec protein gene derived from E. coli are expressed in these transformants, and methods of secretory production of the proteins in which said E. coli transformants are cultured, wherein the proteins are produced and secreted in the periplasm of the E. coli cells.

According to the present invention, useful proteins, such as 20K hGH, whose secretory production has been difficult in microorganisms, can be secreted and accumulated efficiently in the periplasm of E. coli transformants. That is, recombinant proteins can be efficiently produced and secreted by co-expressing recombinant protein genes with at least one Sec protein gene selected from the group consisting of genes of proteins involved in protein secration, i.e., genes of SecB, SecD/F, SecG and SecE/Y, under conditions to suppress excessive expression of the Sec protein gene.

EXPLANATORY NOTES

Figure 1:
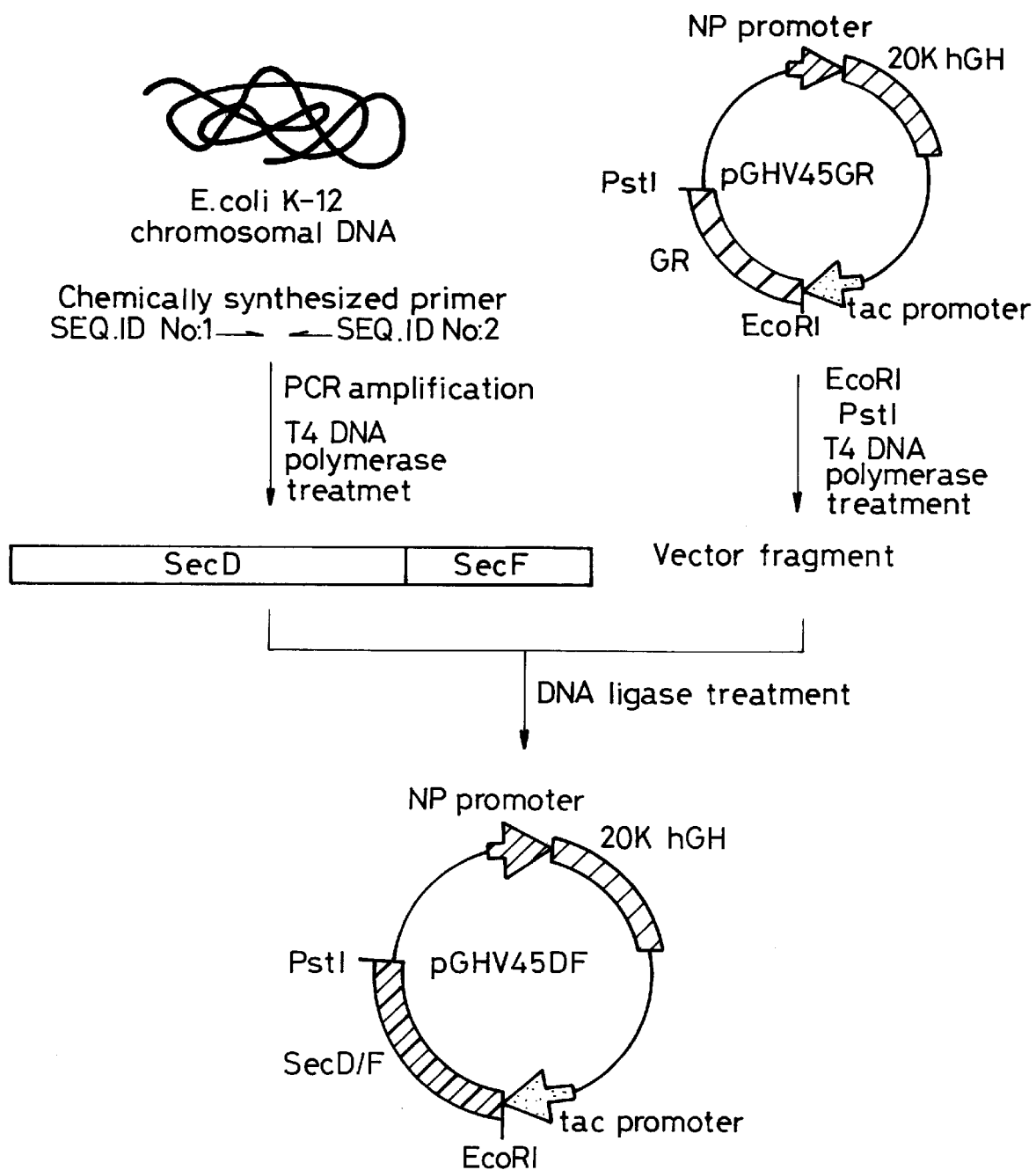
FIG. 1 shows the construction process for the 20K hGH secretion plasmid pGHV45DF for co-expression of 20K hGH gene with SecD/F gene.

SEQ ID NO:1→: Synthesized oligonucleotide primer expressed by SEQ ID NO: 1. The arrow indicates direction of gene synthesis.

←SEQ ID NO:2: Synthesized oligonucleotide primer expressed by SEQ ID NO: 2. The arrow indicates direction of gene synthesis.

SEQ ID NO:3→: Synthesized oligonucleotide primer expressed by SEQ ID NO: 3. The arrow indicates direction of gene synthesis.

← SEQ ID NO:4: Synthesized oligonucleotide primer expressed by SEQ ID NO: 4. The arrow indicates direction of gene synthesis.

SEQ ID NO:5→: Synthesized oligonucleotide primer expressed by SEQ ID NO: 5. The arrow indicates direction of gene synthesis.

← SEQ ID NO:6: Synthesized oligonucleotide primer expressed by SEQ ID NO: 6. The arrow indicates direction of gene synthesis.

← SEQ ID NO:7: Synthesized oligonucleotide primer expressed by SEQ ID NO: 7. The arrow indicates direction of gene synthesis.

SEQ ID NO:8→: Synthesized oligonucleotide primer expressed by SEQ ID NO:8. The arrow indicates direction of gene synthesis.

← SEQ ID NO:9: Synthesized oligonucleotide primer expressed by SEQ ID NO:9. The arrow indicates direction of gene synthesis.

SEQ ID NO:10→: Synthesized oligonucleotide primer expressed by SEQ ID NO: 10. The arrow indicates direction of gene synthesis.

SEQ ID NO:11→: Synthesized oligonucleotide primer expressed by SEQ ID NO: 11. The arrow indicates direction of gene synthesis.

← SEQ ID NO:12: Synthesized oligonucleotide primer expressed by SEQ ID NO: 12. The arrow indicates direction of gene synthesis.

SEQ ID NO:13←: Synthesized oligonucleotide primer expressed by SEQ ID NO: 13. The arrow indicates direction of gene synthesis.

→SEQ ID NO:14: Synthesized oligonucleotide primer expressed by SEQ ID NO: 14. The arrow indicates direction of gene synthesis.

SEQ ID NO:15→: Synthesized oligonucleotide primer expressed by SEQ ID NO: 15. The arrow indicates direction of gene synthesis.

←SEQ ID NO:16: Synthesized oligonucleotide primer expressed by SEQ ID NO: 16. The arrow indicates direction of gene synthesis.

NP promoter: Promoter region of the neutral protease gene of Bacillus amyloliquefaciens 20K hGH: Human growth hormone gene having a molecular weight of about 20,000

GR: Glutathione reductase gene tac promoter: tac promoter region
lacIq: lacIq gene
prlA4-a: DNA fragment obtained by the recognition with restriction endonucleases XhoI and NheI when prlA4 gene was cloned into three separate DNA fragments
prlA4-b: DNA fragment obtained by the recognition with restriction endonucleases NheI and BclI when prlA4 gene was cloned into three separate DNA fragments
prlA4-c: DNA fragment obtained by the recognition with restriction endonucleases BclI and EcoT22I when prlA4 gene was cloned into three separate DNA fragments

DETAILED DESCRIPTION OF THE INVENTION AND PREFERRED EMBODIMENTS

The present invention will be explained in detail as follows.

The proteins involved in membrane transport of proteins (Sec proteins) in the present invention denote in particular SecB, SecE, SecY, SecD, SecF and SecG derived from *E. coli* and variants having the same function as those above, in which one or more amino acid residues are partially inserted, replaced or deleted (for example, a Sec Y variant, i.e., prlA4). Genes of these Sec proteins (Sec protein gene) can be obtained, for example, from *E. coli* chromosomal DNA or the like by methods described under Examples; however, any other method including chemical synthesis can be used.

Sec protein genes primarily reside in the *E. coli* chromosome. However, in the present invention, for example, a Sec protein gene derived from *E. coli* is placed in a plasmid to be expressed independently from a Sec protein gene primarily residing in *E. coli* chromosomal DNA for an artificial expression of the Sec protein gene.

In the present invention, a method in which both genes are present in the same plasmid is used for co-expression of a Sec protein gene and a target protein gene; however, a method in which both genes coexist on a chromosomal DNA or a method in which each gene exists separately on a chromosomal DNA and a plasmid or on two different plasmids may be used.

Suppression of excessive expression of a Sec protein gene in the present invention is carried out by transcriptional suppression or translational suppression. Examples of methods to suppress transcription include a method in which an inducible promoter (e.g., tac promoter or lac promoter) is used for Sec protein gene expression and culturing is carried out with an inducing agent at a low concentration or without an inducing agent, and a method in which a repressor gene (e.g., lacIq gene for tac promoter) as described in Examples 1 to 4 is used. Examples of methods to repress translation include a method in which the number of bases (i.e., distance) from an SD sequence involved in expression of a Sec protein gene, up to the translational initiation codon of the Sec gene is increased.

In the present invention, excessive expression of a Sec protein gene can be readily confirmed by electrophoresis analysis of the fluid obtained by cell destruction of *E. coli* culture.

The present inventors also did studies on SecA, but could not find any secretion promoting effect by co-expression. However, it is highly possible that such an effect by could be found if the co-expression conditions are studied more intensively.

As for the target protein (useful protein) obtained by secretory production by the present invention, any protein which can be secreted in *E. coli* cells can be used; however, proteins derived from eucaryotes, particularly mammals, are especially appropriate. Secretory production of proteins derived from eucaryotes in *E. coli* cells is known to be more difficult than that of proteins derived from procaryotes. This is probably because proteins derived from eucaryotes are recognized as foreign matter when they are expressed in *E. coli* cells, and so they tend to be susceptible to proteolysis. Furthermore, secreted proteins of eucaryote origin undergo incorrect folding upon membrane penetration, which tends to cause protein inactivation. Furthermore, upon secretion, signal peptides cannot always be correctly processed so that it is difficult to obtain proteins having correct N-terminal amino acid sequences. These problems make secretory production of proteins derived from eucaryotes difficult. These problems are attributed to the fact that proteins derived from eucaryotes, whose membrane transport machinery is different from that of procaryotes, are secreted via a membrane transport machinery of procaryotes. Therefore, in secretory production of proteins derived from procaryotes, such as β-lactamase derived from *E. coli*, the co-expression of Sec protein gene is not significant because the protein is secreted through the membrane transport machinery authentic for the protein. On the other hand, in secretory production of proteins derived from mammals in procaryote cells, the effect of co-expression of Sec protein gene is remarkable. Examples of mammalian proteins to be applicable for secretory production in the present invention include G-CSF, insulin, growth hormone, parathyroid hormone (PTH), prolactin and GH binding protein. In particular, human growth hormone having a molecular weight of about 20,000 (hereinafter referred to as 20K hGH) is appropriate because its secretion is markedly effective.

The present inventors had previously established a process for the production of 20K hGH in *E. coli* and obtained a modified signal peptide which has a sequence preferable to that of the original signal peptide involved in secretion of the neutral protease in *Bacillus amyloliquefaciens* in the secretory production of 20K hGH. In order to study the effect of co-expression of a Sec protein gene on secretion efficiency of 20K hGH, the present inventors constructed plasmids from plasmid pGHR10 having this modified signal peptide sequence (this plasmid can be extracted from a 20K hGH secretion *E. coli* strain, MT-10765, FERM BP-5020) as described under Examples, and then transformed *E. coli* cells with the resultant plasmids to compare the efficiency of secretory production of the resultant *E. coli* transformants. In order to improve the secretion efficiency, it is effective to co-express a Sec protein involved in the rate-determining step in a series of processes for protein secretion. Since the rate-determining step differs as a function of the target protein to be secreted, secretion efficiency of all kinds of secretory proteins can be improved by selecting the Sec protein involved in the rate-determining step for each target protein, and co-expressing it while appropriately suppressing the level of expression of the Sec protein. As described under Examples, the fact that co-expression of several Sec protein genes was effective in secretion of 20K hGH implies the presence of multiple rate-determining steps in secretion of 20K hGH, which is considered to be one of the reasons why 20K hGH is difficult to be secreted.

20K hGH has 176 amino acids in its sequence, and arises from a deletion of 15 amino acid residues from the 32nd to the 46th of the 191 amino acids comprising human growth hormone having a molecular weight of about 22,000 (hereinafter referred to as 22K hGH) in clinical use today. 20K hGH has a lower potential for glucose intolerance induction or leukemogenesis, which are suggested to be risk factors in the administration of 22K hGH, and from its biological features, it could be a promising protein for a new human growth hormone drug.

Furthermore, two different amino acids, serine and methionine, are reported for the 14th amino acid from the N-terminal amino acid sequence of 20K hGH. Masuda, N. et al. (Biophysica Acta, 949, 125, 1988) reported that the cDNA base sequence coding for the 14th amino acid from the N terminal is AGT (a code for serine) while Martial, J. A. et al. (Science, 205, 602, 1979) reported that the mRNA base sequence coding for the 14th amino acid from the N terminal is AUG (a code for methionine). In the present invention, 20K hGH denotes both proteins having either methionine or serine as the 14th amino acid of the sequence. Also, 20K hGH of the present invention includes those having an amino acid sequence with one or two replacements, deletions or insertions.

Recombinant plasmids of the present invention can be constructed without difficulty according to conventional methods, for example, by cleaving both ends of a DNA fragment of an obtained gene with restriction endonucleases and by inserting it into an appropriate site of a plasmid amplifiable in E. coli cells. Examples of plasmid vectors to be used for this method include pBR322 and pUCl9, which are commercial products and readily available.

Any E. coli strain can be used as the host in the present invention; however, strains which are not pathogenic and are used ubiquitously are preferable, such as, JM109, HB101 and W3110 (ATCC 27325).

E. coli transformants of the present invention are obtained, for example, by a method in which competent cells are prepared from host E. coli cells by the rubidium chloride method or calcium chloride method, the resultant competent cells and plasmids are mixed, the mixture is exposed in a fluid at high temperature (42° C.) for 60–90 seconds for incorporation of the plasmids into the competent cells, the fluid containing the cells is evenly spread on a plate medium containing a drug (e.g., tetracycline), the plate is incubated, and then colonies formed on the plate medium are recovered.

Thus, recombinant proteins can be efficiently produced and secreted by co-expressing a Sec protein gene with a recombinant protein gene. In secretory production of 20K hGH, co-expression of multiple Sec genes is effective. Examples of E. coli strains for co-expression of individual Sec protein genes in 20K hGH secretory production in the present invention include MT-10827 for SecY/SecE, MT-10823 (FERM BP-5830) for prlA4/SecE, MT-10824 (FERM BP-5831) for SecB, MT-10825 (FERM BP-5832) for SecG and MT-10826 (FERM BP-5833) for SecD/F. The amount of 20K hGH secreted in the cells of these E. coli strains was 50–60 mg per one liter of culture, and the secretion efficiency was about 1.6–2.0 times greater than that with strains without co-expression of Sec protein genes.

Transformed E. coli cells of the present invention can be cultured according to known culture methods or their modified methods in a medium containing carbon and nitrogen sources utilizable by the cells and inorganic salts or their modified medium. Liquid culture is preferable. Examples of preferable media include a 2-fold concentrated LB medium (20 g/l polypeptone, 10 g/l yeast extract) supplemented with 0.2–1.0% glycerol.

By culturing E. coli transformants of the present invention, a secretory protein is secreted and accumulated in the periplasm of cells of the transformants. Preparation of the secretory protein from the periplasm of these E. coli transformants can be carried out by an ordinary method of recovering and purifying proteins from the periplasm. For example, an osmotic pressure shock method (Nossal, G. N., J. Biol. Chem., 241(13), 3055–3062, 1966) can be used.

The present invention will be illustrated in detail by the following examples; however, the invention is not intended to be limited to these examples.

The "co-expression" in the following Examples means that one or more Sec genes and the 20K hGH gene are artificially co-expressed.

EXAMPLE 1

Effect of co-expression of SecD/F gene on secretion efficiency of 20K hGH (1) Construction of 20K hGH secretion plasmid pGHV45DF for expression of SecD/F gene by tac promoter The process for construction is shown in FIG. 1. Using the chromosomal DNA of Escherichia coli K-12 strain (ATCC 23716) as a template, an operon containing SecD/F gene was amplified by the PCR method using synthesized oligonucleotide primers of SEQ ID NO:1 and SEQ ID NO:2 to obtain a DNA fragment of about 2.9 kb containing SecD/F gene. This obtained DNA fragment was treated with T4 DNA polymerase to obtain a blunt-ended insert fragment. Next, a 20K hGH expression plasmid pGHV45GR (this plasmid was obtained from plasmid pGHR10 by cleaving it with restriction endonucleases EcoT14I and AvaI, then ligating the resulting larger DNA fragment to remove the lacIq gene segment) was digested with restriction endonucleases EcoRI and PstI, and the resultant fragment was treated with T4 DNA polymerase to obtain a blunt-ended vector fragment. This vector fragment was ligated in the presence of the abovementioned insert fragment to construct a 20K hGH secretion plasmid pGHV45DF for co-expression of E. coli SecD/F gene.

(2) Secretory production by E. coli transformants transformed by pGHV45DF

Cells of E. coli HB101 strain and JM109 strain were transformed by the pGHV45DF constructed in (1) above, the resultant transformants were inoculated onto an LB agar medium supplemented with 10 μg/ml tetracycline, and incubation was carried out at 30° C. overnight to obtain colonies. Isolated transformants were individually cultured in a 2-fold concentrated LB medium (20 g/l polypeptone, 10 g/l yeast extract) supplemented with 10 μg/ml tetracycline at 30° C. for 24 hours.

Since expression of the SecD/F gene on the plasmid pGHV45DF is associated with the transcription mechanism by the tac promoter, the effect of expression of the SecD/F gene on 20K hGH secretion was studied for transformants of both E. coli strains with and without the addition of IPTG (1 mM) at the start of incubation, as follows: After culturing transformants of both E. coli strains, 20K hGH secreted and accumulated in the periplasm was recovered by the osmotic shock method, and 20K hGH concentrations in the periplasm fluid fractions were measured by enzyme-immunoassay using an antibody against a human growth hormone (Kato, K. et al., J. Immunol., 116, 1554, 1976). The periplasm fractions were prepared as follows: First, cells were recovered by centrifuging the culture, then suspended in an isotonic solution (10 mM tris-HCl buffer containing 20% sucrose and 1 mM EDTA, pH 7.0) of a ¹/₁₀ volume of original culture. The suspension was allowed to stand for 30 minutes and then centrifuged to recover the cells. Next, the recovered cells were re-suspended in cold water (4° C.) of a ¹/₁₀ volume of original culture, and then the suspension was centrifuged again to recover 20K hGH, which has been secreted and accumulated in the periplasm, in the supernatant. The 20K hGH concentration of this periplasm fraction was measured by the abovementioned enzyme immunoassay, and the amount of secreted 20K hGH (mg) per 1 litter of culture was calculated from the measurements. Results are shown in Table 1.

TABLE 1

Effect of co-expression of SecD/F on 20K hGH secretion (mg/l culture)

| Host E. coli strain | HB101 | | JM109 | |
|---|---|---|---|---|
| IPTG (1 mM) | — | + | — | + |
| 20K hGH secretion | 18 | 10 | 62 | 20 |

In JM109 transformants, 20K hGH secretion was significantly high in the absence of induction by the addition of IPTG, while in HB101 transformants, 20K hGH secretion was low both with and without the addition of IPTG.

The difference in the effect of co-expression of SecD/F gene on secretion of 20K hGH in the transformants of the different strains was considered to be due to the fact that JM109 strain has the lacIq gene (a repressor gene for tac promoter) while HB101 strain has no lacIq gene. Namely, the present inventors made a hypothesis as follows: Since HB101 has no lacIq gene, the SecD/F gene is excessively expressed by tac promoter independently of the addition of IPTG; therefore, efficiency of 20K hGH secretion is not improved. On the other hand, in JM109 which has the lacIq gene, the SecD/F gene expressed by tac promoter is excessively produced under inductive conditions with the addition of IPTG so that 20K hGH secretion cannot be promoted, while excessive expression of the SecD/F gene is suppressed under non-inductive conditions so that 20K hGH secretion efficiency can be improved.

Based on this hypothesis, 20K hGH secretion was studied in transformants made by transforming cells of HB 101 strain, which has primarily no lacIq gene, by a plasmid containing SecD/F gene and 20K hGH gene with the incorporated lacIq gene.

Figure 2:
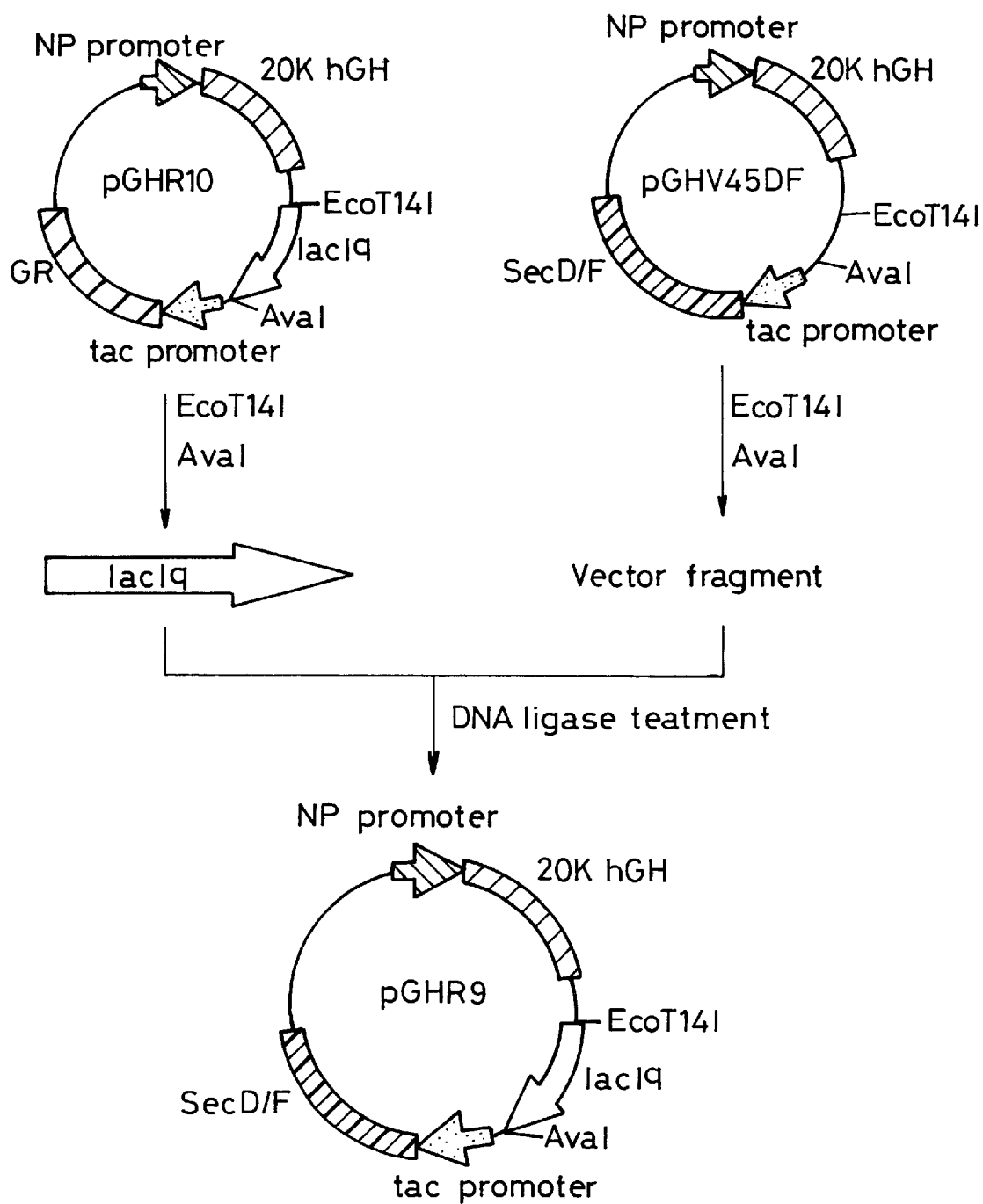
FIG. 2 shows the construction process of the 20K hGH secretion plasmid pGHR9 for co-expression of 20K hGH gene with SecD/F gene while suppressing excessive expression of SecD/F gene by the lacIq gene.

(3) Construction of 20K hGH secretion plasmid pGHR9 for suppression of excessive expression of SecD/F gene by lacIq gene The process for construction is shown in FIG. 2. 20K hGH secretion plasmid pGHR10 was extracted from a 20K hGH secretion E. coli strain MT-10765 (FERM BP-5020), and digested with restriction endonucleases EcoT14I and AvaI to obtain a DNA fragment of about 1.1 kb containing the lacIq gene. Next, the abovementioned pGHV45DF was digested with restriction endonucleases EcoT14I and AvaI to obtain a vector fragment. This vector fragment was ligated in the presence of the abovementioned DNA fragment containing the lacIq gene to construct the 20K hGH secretion plasmid pGHR9 capable of suppressing excessive expression of SecD/F gene by the lacIq gene. Using this plasmid, cells of E. coli HB101 strain (purchased from Takara Shuzo Co., Ltd.) were transformed to obtain a transformed E. coli strain of MT-10826 (FERM BP-5833).

(4) Secretory production of 20K hGH using pGHR9

Cells of E. coli HB101 strain were transformed by 20K hGH secretion plasmid pGHV45 exhibiting no co-expression of Sec gene (this plasmid was obtained from plasmid pGHR10 by digesting it with restriction endonucleases EcoT14I and AccIII, then ligating the resulting larger DNA fragment to remove a lacIq gene segment and a glutathione reductase expression gene segment) to obtain a transformed strain MT-10829. Cells of this transformed strain MT-10829 and the transformed strain MT-10826 obtained by transforming E. coli HB101 by pGHR9 constructed in (3) were cultured in the same manner as described in (1) to compare 20K hGH secretion. Results are shown in Table 2.

TABLE 2

Effect of co-expression of SecD/F gene on 20K hGH secretion (mg/l culture)

| Name of strain | MT-10829 | | MT-10826 | |
|---|---|---|---|---|
| Name of plasmid | pGHV45 | | pGHR9 | |
| Co-expression protein | None | | SecD/F | |
| IPTG (1 mM) | — | | — | + |
| 20K hGH secretion | 33 | | 64 | 19 |

Results revealed that when excessive expression of SecD/F gene was suppressed by lacIq, the amount of secretion of 20K hGH was about 1.9 times greater than that with no co-expression of Sec protein gene.

Conversely, when expression of SecD/F gene was promoted by the addition of IPTG, secretion of 20K hGH was decreased.

Thus, in the case of the SecD/F gene, secretion of 20K hGH was greatly improved in cells of E. coli HB101 strain transformed by the 20K hGH secretion plasmid in which tac promoter was used as an expression promoter and excessive expression was suppressed by lacIq. Accordingly, similar methods were used to study the effect of co-expression of other Sec protein genes derived from E. coli as described below.

EXAMPLE 2

Figure 3:
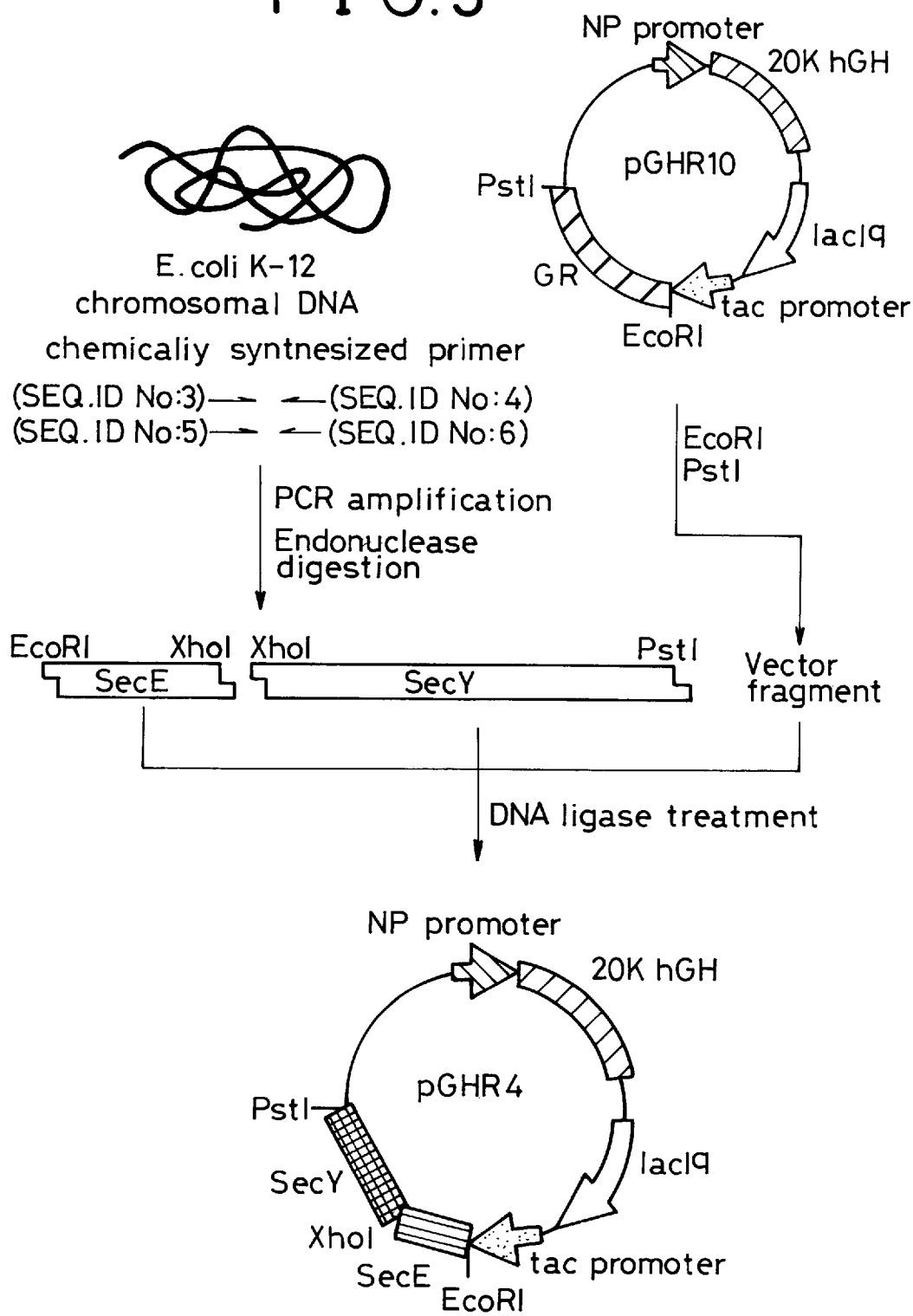
FIG. 3 shows the construction process of the 20K hGH secretion plasmid pGHR4 for co-expression of 20K hGH gene with SecE/Y gene while suppressing excessive expression of SecE/Y gene by the lacIq gene.

Effect of co-expression of SecE/Y gene on 20K hGH secretion efficiency (1) Construction of secretion plasmid pGHR4 for co-expression of 20K hGH gene and SecE/Y gene The process for construction is shown in FIG. 3. Using the chromosomal DNA of Escherichia coli K-12 strain (ATCC 23716) as a template, SecE and SecY genes were individually amplified by the PCR method using synthesized oligonucleotide primers of SEQ ID NO:3 together with SEQ ID NO:4, and SEQ ID NO:5 together with SEQ ID NO:6 (Mullis, K. B. et al., Methods Enzymol., 155, 335–350, 1987), respectively. The resultant two DNA fragments were each digested with restriction endonucleases using the restriction sites at both ends (EcoRI, XhoI and PstI) to obtain a DNA fragment of about 0.4 kb coding for SecE gene and a DNA fragment of about 1.3 kb coding for Sec Y gene. Next, plasmid pGHR10 was digested with restriction endonucleases EcoRI and PstI, and the isolated DNA fragment of about 6.0 kb was treated with ligase in the presence of the abovementioned DNA fragments of about 0.4 kb and about 1.3 kb to construct the 20K hGH secretion plasmid pGHR4 for co-expression of the SecE/Y gene. In this step, the insert fragments, i.e., the DNA fragments of about 0.4 kb and about 1.3 kb, were bonded at the XhoI restriction site. In this expression system, mRNAs for SecE and SecY genes are transcribed by tac promoter. An SD sequence consisting of AGGA was inserted at 9 and 4 bases upstream from the translation initiation points of SecE and SecY genes, respectively, for the coordination of the amino acid codon frames. Using this plasmid, cells of E. coli HB101 strain (purchased from Takara Shuzo, Co., Ltd.) were transformed by the method of Inoue, H. et al. (Gene, 96, 23–28, 1990) to obtain a transformed E. coli strain MT-10827.

Figure 4:
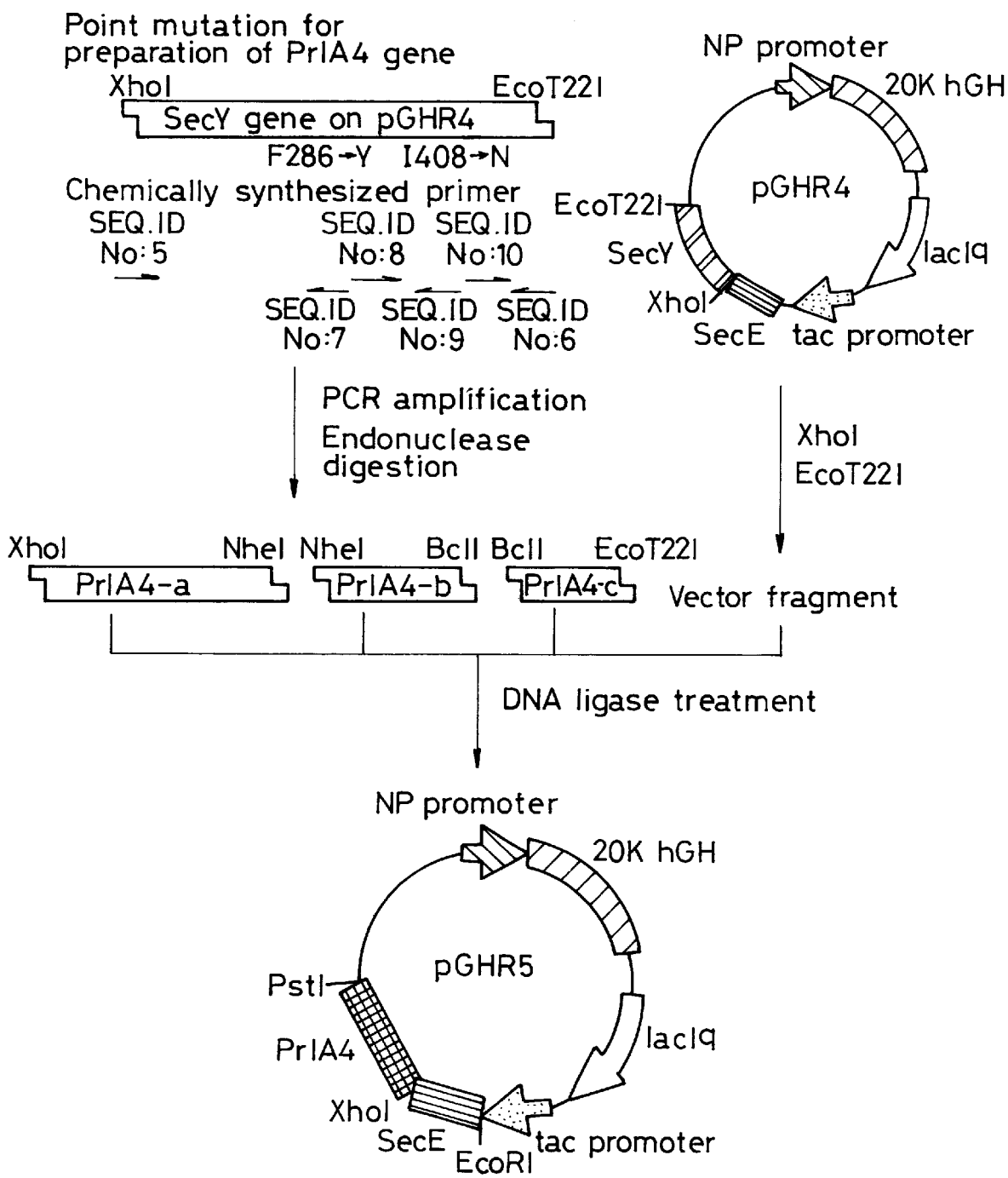
FIG. 4 shows the construction process of the 20K hGH secretion plasmid pGHR5 for co-expression of 20K hGH gene with prlA4/SecE gene while suppressing excessive expression of prlA4/SecE gene by the lacIq gene.

(2) Construction of secretion plasmid pGHR5 for co-expression of 20K hGH gene and prlA4/SecE gene The process for construction is shown in FIG. 4. First, primers for the substitution of the mutation points of prlA4, i.e., F286 and I408, by Y286 and N408 (F:Phe, I:Ile, Y:Tyr, N:Asn), respectively, were constructed (SEQ ID NO:7 to SEQ ID NO:10). Using these primers and primers for SecY gene cloning (SEQ ID NO:5 and SEQ ID NO:6), PCR amplification using pGHR4 as a template was carried out for preparation of prlA4 gene from Sec Y gene. This PCR amplification cloned the prlA4 gene into three separate DNA fragments. These three fragments were each treated with appropriate restriction endonucleases (XhoI, NheI, BclI and EcoT22I) as shown in FIG. 4 to obtain DNA fragments (prlA4-a, prlA4-b and prlA4-c). On the other hand, plasmid pGHR4 was digested with restriction endonucleases XhoI and EcoT22I to obtain a vector fragment. This vector fragment was treated with ligase in the presence of an excessive amount of the abovementioned three DNA fragments to construct 20K hGH secretion plasmid pGHR5 for co-expression of prlA4/SecE gene. Using this pGHR5, cells of *E. coli* HB101 strain were transformed (purchased from Takara Shuzo, Co., Ltd.) were transformed to obtain the MT-10823 strain (FERM BP-5830).

(3) Secretory production of 20K hGH using pGHR4 and pGHR5

Cells of MT-10829 strain, which was made by transforming *E. coli* HB101 strain by 20K hGH secretion plasmid pGHV45 exhibiting no co-expression of Sec protein genes, and cells of MT-10827 and MT-10823 strains, which were made by transforming *E. coli* HB101 strain by plasmids pGHR4 and pGHR5 obtained in (1) and (2) above, respectively, were each inoculated onto an LB agar medium supplemented with 10 μg/ml tetracycline. Incubation was carried out at 30° C. overnight to get colonies. Resultant isolated transformants were each cultured in a 2-fold concentrated LB medium (20 g/l polypeptone, 10 g/l yeast extract) supplemented with 10 μg/ml tetracycline at 30° C. for 24 hours, without the addition of IPTG. After incubation, periplasm fluid fractions were prepared in the same manner as described in Example 1, and the 20K hGH concentration in the periplasm fluid fraction was measured. Results are shown in Table 3.

TABLE 3

Effect of co-expression of SecE/Y gene and PrlA4/SecE gene on 20K hGH secretion (mg/l culture)

| Name of strain | MT-10829 | MT-10827 | MT-10823 |
|---|---|---|---|
| Name of plasmid | pGHV45 | pGHR4 | pGHR5 |
| Co-expression protein | None | SecE/Y | PrlA4/SecE |
| 20K hGH secretion | 33 | 50 | 62 |

The level of 20K hGH secretion with co-expression of SecE/Y gene was 1.6 times greater than that without co-expression of Sec protein genes. Furthermore, the level of secretion with co-expression of prlA4/SecE gene was about 1.8 times greater than that without co-expression of Sec protein genes.

Figure 5:
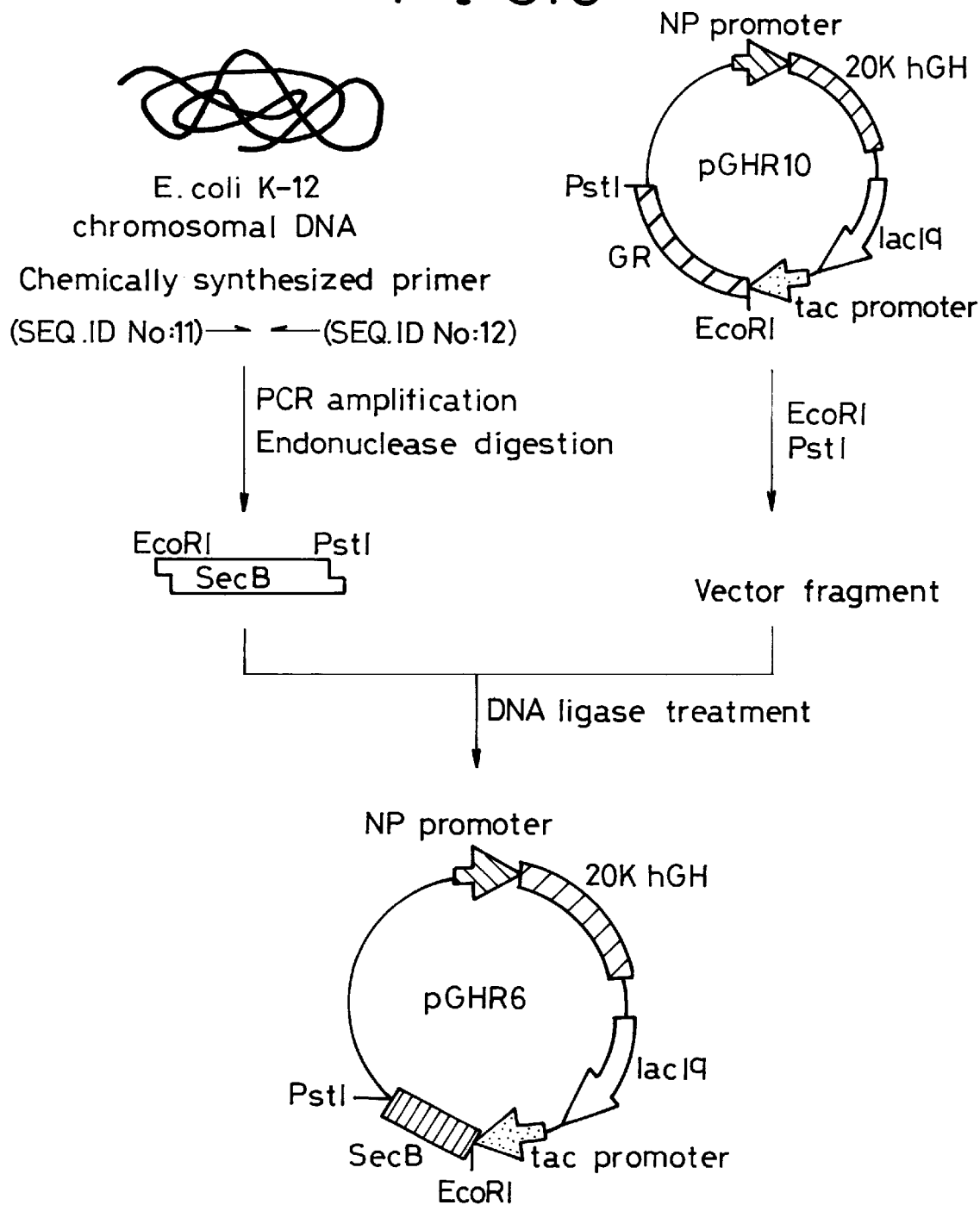
FIG. 5 shows the construction process of the 20K hGH secretion plasmid pGHR6 for co-expression of 20K hGH gene with SecB gene while suppressing excessive expression of SecB gene by the lacIq gene.

EXAMPLE 3
Effect of co-expression of SecB gene on 20K hGH secretion efficiency (1) Construction of secretion plasmid pGHR6 for co-expression of 20K hGH gene and SecB gene The process for construction is shown in FIG. 5. Using the chromosomal DNA of *Escherichia coli* K-12 strain (ATCC 23716) as a template, SecB gene was amplified by the PCR method using synthesized oligonucleotide primers of SEQ ID NO:11 and SEQ ID NO:12 to obtain a DNA fragment of about 0.5 kb containing SecB gene. This fragment was digested with restriction endonucleases at the restriction sites of both ends (EcoRI and PstI) to obtain an insert fragment. Next, plasmid pGHR10, which was extracted from an *E. coli* strain for 20K hGH secretion production, MT-10765, was digested with restriction endonucleases EcoRI and PstI, and the isolated DNA fragment of about 6.0 kb was treated with ligase in the presence of the abovementioned insert fragment to construct the 20K hGH secretion plasmid pGHR6 for co-expression of the SecB gene. Using this plasmid pGHR6, cells of *E. coli* HB101 strain (purchased from Takara Shuzo, Co., Ltd.) were transformed by the method of Inoue, H. et al. (Gene, 96, 23–28, 1990) to obtain a transformed *E. coli* strain, MT-10828.

(2) Secretory production of 20K hGH using pGHR6

Cells of MT-10829 strain, which was made by transforming *E. coli* HB101 strain with 20 K hGH secretion plasmid pGHV45 exhibiting no co-expression of Sec protein genes, and cells of MT-10828 strain, which was made by transforming *E. coli* HB101 strain with pGHR6 obtained in (1) above, were inoculated in the same manner as described in Example 2, and 20K hGH secretion was compared. Results are shown in Table 4.

TABLE 4

Effect of co-expression of SecB gene on 20K hGH secretion (mg/l culture)

| Name of strain | MT-10829 | MT-10828 |
|---|---|---|
| Name of plasmid | pGHV45 | pGHR6 |
| Co-expression protein | None | SecB |
| 20K hGH secretion | 33 | 43 |

20K hGH secretion was significantly increased when 20K hGH was co-expressed by suppressing excessive expression of SecB gene by the lacIq gene. However, analysis of the fluid obtained by ultrasonic destruction of the cells in the culture by SDS-PAGE revealed that SecB protein (molecular weight: 16 KDa) had been expressed in abundance. Accordingly, the inventors thought that 20K hGH secretion was not sufficient because of the insufficient suppression of SecB gene expression, and decided to construct a co-expression plasmid for a further suppression of the excessive expression of SecB gene.

Figure 6:
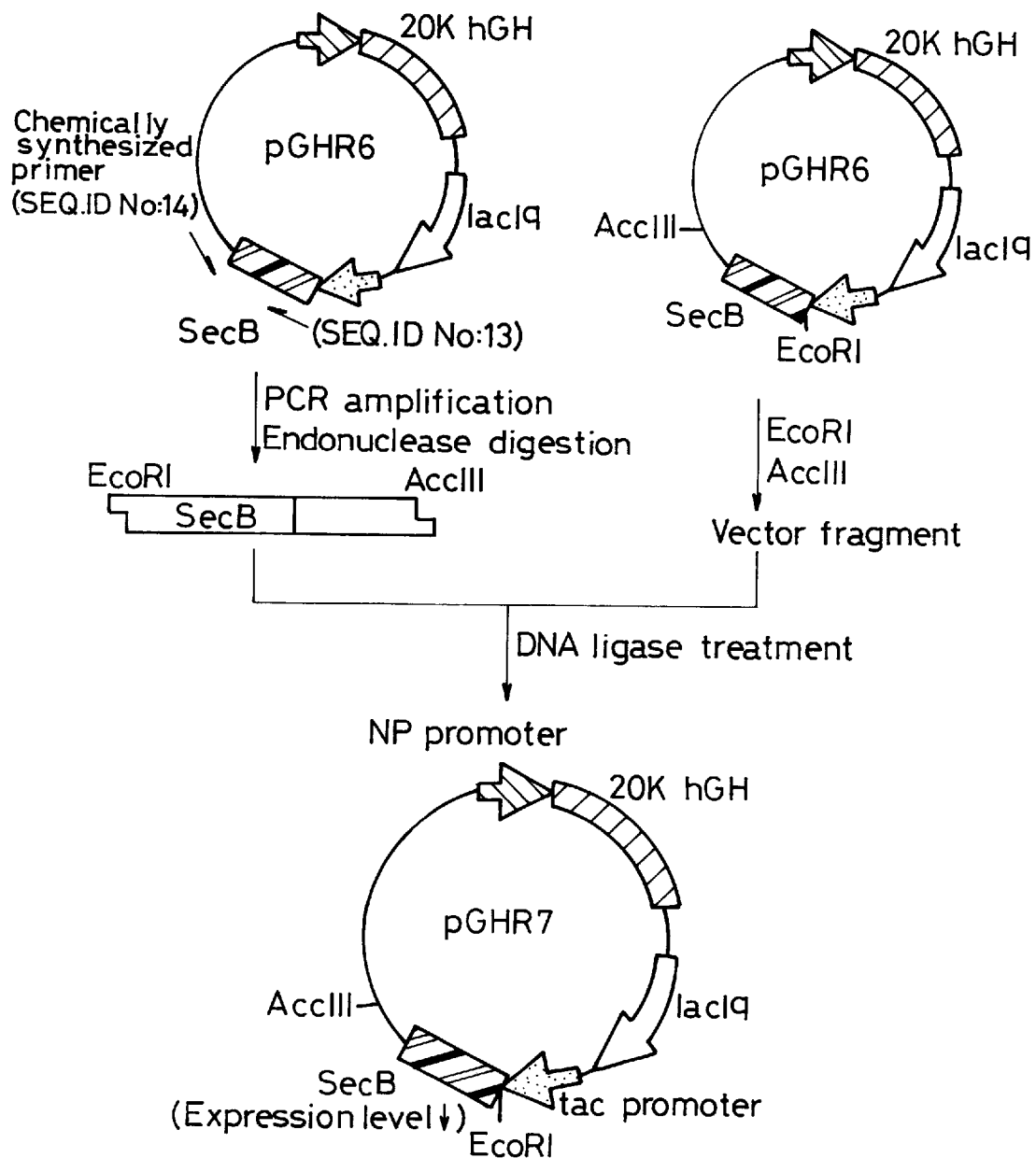
FIG. 6 shows the construction process of the 20K hGH secretion plasmid pGHR7 for co-expression of 20K hGH gene with SecB gene while strongly suppressing excessive expression of SecB gene by the lacIq gene as well as by extending the distant from the SecB gene translation initiation site to the SD sequence.

(3) Construction of secretion plasmid pGHR7 for co-expression of 20K hGH gene and appropriate level of SecB gene The process for construction is shown in FIG. 6. For further suppression of excessive expression of SecB gene, the distance from the SD sequence derived from pKK223-3 to the translation initiation codon was extended. Specifically, the distance, which was 10 bp in the abovementioned pGHR6, was extended to 50 bp, and PCR amplification was carried out using pGHR6 plasmid as a template using PCR primers (SEQ ID NO:13 and SEQ ID NO:14) to insert the SD sequence derived from SecB gene at 10 bp upstream of the translation initiation codon. Thus, a DNA fragment of about 1.2 kb containing SecB gene with the transformed SD sequence was obtained. This fragment was digested with endonucleases EcoRI and AccIII at the restriction sites of both ends to obtain an insert fragment. Next, plasmid pGHR6 was digested with restriction endonucleases EcoRI and AccIII to obtain a vector fragment. This vector fragment was treated with ligase in the presence of the abovementioned insert fragment to construct the 20K hGH secretion plasmid pGHR7 for regulation of excessive expression of SecB gene. Using this plasmid, cells of E. coli HB101 strain (purchased from Takara Shuzo, Co., Ltd.) were transformed to obtain a transformed E. coli strain, MT-10824 (FERM BP-5831).

(4) Secretory production of 20K hGH using pGHR7

Cells of MT-10829 strain, which was made by transforming E. coli HB101 strain with 20 K hGH secretion plasmid pGHV45 exhibiting no co-expression of Sec protein gene, and MT-10824 strain, which was made by transforming E. coli HB101 strain by the pGHR7 obtained in (3) above, were cultured in the same manner as described in Example 1, and 20K hGH secretion was compared. Results are shown in Table 5.

TABLE 5

Effect of co-expression of SecB gene on 20K hGH secretion (2) (mg/l culture)

| Name of strain | MT-10829 | MT-10824 |
|---|---|---|
| Name of plasmid | pGHV45 | PGHR7* |
| Co-expression protein | None | SecB |
| 20K hGH secretion | 33 | 63 |

*This plasmid suppresses SecB gene expression greater than PGHR6.

Results revealed that when co-expression of SecB gene was suppressed to an appropriate extent, the level of 20K hGH secretion was 1.8 times greater than that without co-expression of Sec protein genes.

Further, the decrease in the level of SecB gene repression was confirmed by SDS-PAGE.

EXAMPLE 4

Figure 7:
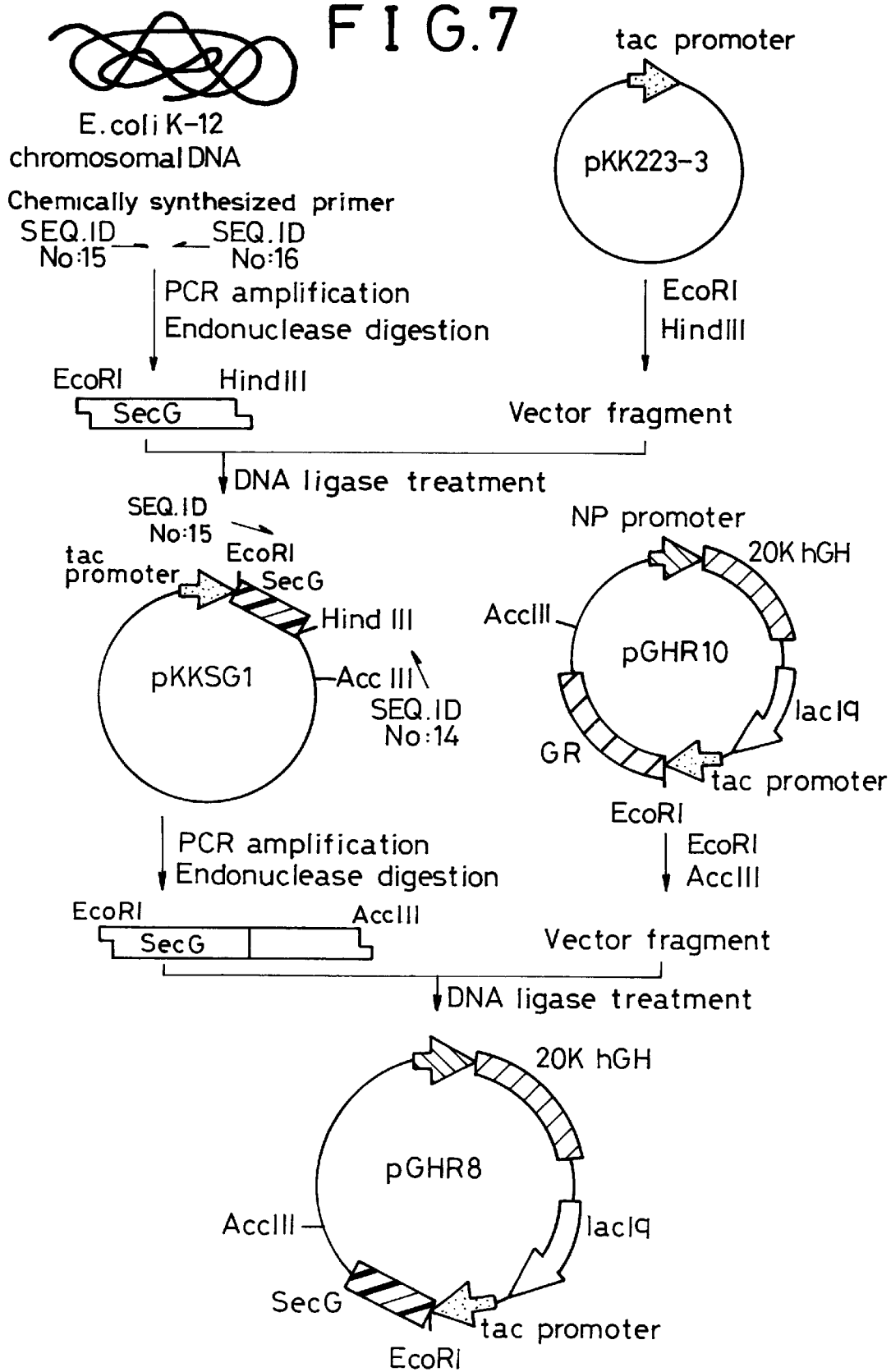
FIG. 7 shows the construction process of the 20K hGH secretion plasmid pGHR8 for co-expression of 20K hGH gene with SecG gene while suppressing excessive expression of SecG gene by the lacIq gene.

Effect of co-expression of SecG gene on 20K hGH secretion efficiency (1) Construction of secretion plasmid pGHR8 for co-expression of 20K hGH gene and SecG gene The process for construction is shown in FIG. 7. Using the chromosomal DNA of Escherichia coli K-12 strain (ATCC 23716) as a template, SecG gene was amplified by the PCR method using synthesized oligonucleotide primers of SEQ ID NO:15 and SEQ ID NO:16 to obtain a DNA fragment of about 0.3 kb containing the SecG gene. This fragment was digested with restriction endonucleases at the restriction sites of both ends (EcoRI and HindIII) to obtain an insert fragment. This insert fragment was cloned between restriction sites EcoRI and HindIII of an expression plasmid pKK223-3 purchased from Pharmacia to construct pKKSG1. Subsequently, in order to incorporate a SecG expression region into a 20K hGH expression plasmid, PCR amplification was carried out using this pKKSG1 as a template using SEQ ID NO:14 and SEQ ID NO:15, and then digestion with EcoRI and AccIII was carried out to prepare an insert fragment. Next, 20K hGH expression plasmid pGHR10 was digested with restriction endonucleases EcoRI and AccIII, and the isolated DNA fragment was treated with ligase in the presence of the abovementioned insert fragment to construct the 20K hGH secretion plasmid pGHR8 for co-expression of the SecG gene. Using this plasmid, cells of E. coli HB101 strain (purchased from Takara Shuzo, Co., Ltd.) were transformed to obtain the transformed E. coli MT-10825 strain (FERM BP-5832).

(2) Secretory production of 20K hGH using pGHR8

Cells of MT-10829 strain, which was made by transforming E. coli HB101 strain with 20 K hGH secretion plasmid pGHV45 exhibiting no co-expression of Sec protein genes, and cells of MT-10825 strain, which was made by transforming E. coli HB101 strain with pGHR8 obtained in (1) above, were cultured in the same manner as described in Example 1, and 20K hGH secretion was compared. Results are shown in Table 6.

TABLE 6

Effect of co-expression of SecG gene on 20K hGH secretion (mg/l culture)

| Name of strain | MT-10829 | MT-10825 |
|---|---|---|
| Name of plasmid | pGHV45 | PGHR8 |
| Co-expression protein | None | SecG |
| 20K hGH secretion | 33 | 58 |

Results revealed that the level of 20K hGH secretion with co-expression of SecG gene was 1.8 times greater than that without co-expression of said genes.

The microorganisms having FERM BP numbers used in the above Examples are deposited under the Budapest Treaty on the following date with the National Institute of Bioscience and Human-Technology of the Agency of Industrial Science and Technology of the Ministry of International Trade and Industry, 1–3, Higashi, 1-chome, Tsukuba-shi, Ibaraki-ken, 305 Japan:

| Strain No. | Accession No. | Deposition Date |
|---|---|---|
| MT-10765 | FERM BP-5020 | February 28, 1995 |
| MT-10823 | FERM BP-5830 | March 7, 1996 |
| MT-10824 | FERM BP-5831 | March 7, 1996 |
| MT-10825 | FERM BP-5832 | March 7, 1996 |
| MT-10826 | FERM BP-5833 | March 7, 1996 |

The primers for PCR used in the above Examples have the following nucleotide sequence:

SEQ ID NO:1 ATCAAGCTTA AGGGAATTGC CGTGT
SEQ ID NO:2 ACTGAGCTCA AATCCCGATC TTCTGA
SEQ ID NO:3 TATGAATTCA TGAGTGCGAA TAC-CGAAGCT CAA
SEQ ID NO:4 AAACTCGAGT CACCTCAGGC CAGT-GATAAA GGA
SEQ ID NO:5 TTTCTCGAGA GGAAACAATG GCTAAACAAC CGGGATTAGA T
SEQ ID NO:6 TTTCTGCAGA TGCATTTATC GGCCG-TAGCC TTTCAGGTT
SEQ ID NO:7 ACTGCTAGCG AAGATTGCCG GGAT
SEQ ID NO:8 TTCGCTAGCA GTATTATTCT GTACCCG
SEQ ID NO:9 CCATGATCAC GACAACAACG TTAAG
SEQ ID NO:10 CGTGATCATG GACTTTATGG CTCAA
SEQ ID NO:11 GTAGAATTCA TGTCAGAACA AAA-CAACACT
SEQ ID NO:12 CCAAGCTTTC TTGCCAGGGT
SEQ ID NO:13 ACAGAATTCC CGGGGATCCG TCGAC-CTGCA GTATTTAAGG ACAACACTTA AGGGTTTTCT ACACATGTCA GAACAAAACA ACACT
SEQ ID NO:14 AGATCCGGAG CAAAAACAGG AAGGC
SEQ ID NO:15 TTTGAATTCC GCAAGGAACA GGTTG
SEQ ID NO:16 TTTAAGCTTT TTAGTTCGGG ATATC

What is claimed is:

1. A recombinant plasmid containing (i) a gene encoding a native human growth hormone or an allelic variant thereof having a molecular weight of about 20,000;

(ii) at least one Sec gene obtained from *Escherichia coli* which Sec gene is selected from the group consisting of SecB, SecD/F, SecG and SecE/Y, wherein the expression of said at least one Sec gene is under the control of an inducible promoter; and (iii) a repressor operably linked to said inducible promoter which provides for suppression of the expression of said Sec protein gene, thereby enhancing the secretory production of said human growth hormone.

2. A recombinant plasmid according to claim 1, wherein said inducible promoter is the tac promoter and the repressor gene operably linked thereto is lacIq.

3. An *Escherichia coli* transformant strain which is obtained by transforming an *E. coli* host strain with a recombinant plasmid according to claim 1 and which transformant strain co-expresses said human growth hormone and said Sec protein obtained from *E. coli*.

4. An *Escherichia coli* transformant strain according to claim 3 wherein said *E. coli* transformant strain is selected from the group consisting of FERM BP-5830, FERM BP-5831, FERM BP-5832 and FERM BP-5833, which strains were deposited at the National Institute of Bioscience and Human-Technology Agency of Industrial Science and Technology, having an address of 1-3, Higashi 1-chome, Tsukuba-shi, Ibaraki-ken, 305 Japan.

5. A method for obtaining secretory production of a human growth hormone having a molecular weight of about 20,000, comprising culturing an *E. coli* transformant strain according to claim 3 to provide for secretory production of a human growth hormone having a molecular weight of about 20,000 in the periplasm of the cultured *E. coli* transformant strain cells.

6. An *Escherichia coli* transformant strain which is obtained by transforming an *E. coli* host strain with a recombinant plasmid according to claim 2.

7. A method for obtaining secretory production of a human growth hormone having a molecular weight of about 20,000, comprising culturing an *E. coli* transformant strain according to claim 6 to obtain secretory production of said human growth hormone in the periplasm of said *E. coli* cells.

8. A method for obtaining secretory production of a human growth hormone having a molecular weight of about 20,000, comprising culturing cells of an *E. coli* transformant strain according to claim 4 to provide for secretory production of said human growth hormone in the periplasm of *E. coli* cells.

* * * * *